(12) United States Patent
Ogura et al.

(10) Patent No.: US 9,216,252 B2
(45) Date of Patent: Dec. 22, 2015

(54) APPLICATOR

(75) Inventors: Makoto Ogura, Tsukuba (JP); Seiji Tokumoto, Tsukuba (JP)

(73) Assignee: Hisamitsu Pharmaceutical Co., Inc., Tosu-shi, Saga (JP)

( * ) Notice: Subject to any disclaimer, the term of this patent is extended or adjusted under 35 U.S.C. 154(b) by 42 days.

(21) Appl. No.: 14/123,523

(22) PCT Filed: Jul. 13, 2012

(86) PCT No.: PCT/JP2012/067918
§ 371 (c)(1),
(2), (4) Date: Dec. 3, 2013

(87) PCT Pub. No.: WO2013/015136
PCT Pub. Date: Jan. 31, 2013

(65) Prior Publication Data
US 2014/0128818 A1    May 8, 2014

(30) Foreign Application Priority Data

Jul. 27, 2011 (JP) ................. P2011-164723

(51) Int. Cl.
*A61M 5/315* (2006.01)
*A61M 37/00* (2006.01)

(52) U.S. Cl.
CPC ....... *A61M 5/31515* (2013.01); *A61M 37/0015* (2013.01); *A61M 2037/0023* (2013.01)

(58) Field of Classification Search
CPC ............... A61M 2037/0023; A61M 2037/003; A61M 2037/0038; A61M 2037/0046; A61M 2037/0053; A61M 2037/0061; A61M 37/0015; A61M 2005/206; A61M 2005/1585; A61M 2005/3287; A61M 2005/2026; A61M 5/2033; A61M 2005/14506; A61M 5/1454

USPC .................................. 604/181–243
See application file for complete search history.

(56) References Cited

U.S. PATENT DOCUMENTS 3,756,242 A    9/1973  Coss
D322,671 S    12/1991  Szwarc
(Continued)

FOREIGN PATENT DOCUMENTS

CN    1454104 A    11/2003
CN    1691969 A    11/2005
(Continued)

OTHER PUBLICATIONS

Search Report issued in International Application No. PCT/JP2012/067918 mailed Aug. 28, 2012, 2 pages.
(Continued)

*Primary Examiner* — Nicholas Lucchesi
*Assistant Examiner* — Morgan Lee
(74) *Attorney, Agent, or Firm* — Nath, Goldberg & Meyer; Joshua B. Goldberg

(57) ABSTRACT

An applicator comprising a transmission member, a housing guiding a reciprocation of the transmission member, and a cap covering the housing. The transmission member is provided with a stopper extending in a direction orthogonal to an axial direction thereof. An upper end of the housing is formed with a projection sliding the stopper. The inside of the cap is formed with a lead part. The stopper is slid by the lead part to an end part of the projection when the cap is pushed and thereafter disengages from the projection when the cap is further pushed, so that the transmission member transmits the biasing force of an elastic member to a microneedle. This enables the microneedle to be applied to skin.

8 Claims, 13 Drawing Sheets

(56) References Cited

U.S. PATENT DOCUMENTS

| | | |
|---|---|---|
| D447,231 S | 8/2001 | Chen Fu et al. |
| D565,732 S | 4/2008 | Pech et al. |
| D612,493 S | 3/2010 | Claessens et al. |
| D613,861 S | 4/2010 | Hunter et al. |
| D627,459 S | 11/2010 | Uchida et al. |
| D655,001 S | 2/2012 | Becker et al. |
| 8,308,697 B2 | 11/2012 | Stamp et al. |
| 2004/0143211 A1 | 7/2004 | Haider et al. |
| 2005/0096586 A1 | 5/2005 | Trautman et al. |
| 2005/0165358 A1 | 7/2005 | Yeshurun et al. |
| 2005/0261631 A1 | 11/2005 | Clarke et al. |
| 2006/0142691 A1 | 6/2006 | Trautman et al. |
| 2007/0265568 A1 | 11/2007 | Tsals et al. |
| 2008/0215001 A1 | 9/2008 | Cowe |
| 2008/0269690 A1 | 10/2008 | Felix-Faure |
| 2009/0227950 A1 | 9/2009 | Jensen et al. |
| 2009/0312717 A1 | 12/2009 | Christiansen |

FOREIGN PATENT DOCUMENTS

| | | |
|---|---|---|
| CN | 101868272 A | 10/2010 |
| JP | 2005533625 A | 11/2005 |
| JP | 2005537058 A | 12/2005 |
| JP | 2007509706 A | 4/2007 |
| JP | 2008534152 A | 8/2008 |
| JP | 2010540059 A | 12/2010 |

OTHER PUBLICATIONS

Office Action issued in Design U.S. Appl. No. 29/411,801 dated Dec. 28, 2012, 8 pages.

European Patent Application No. 12818293.8, Search Report dated Apr. 28, 2015, seven (7) pages.

*Fig.13*
(a)
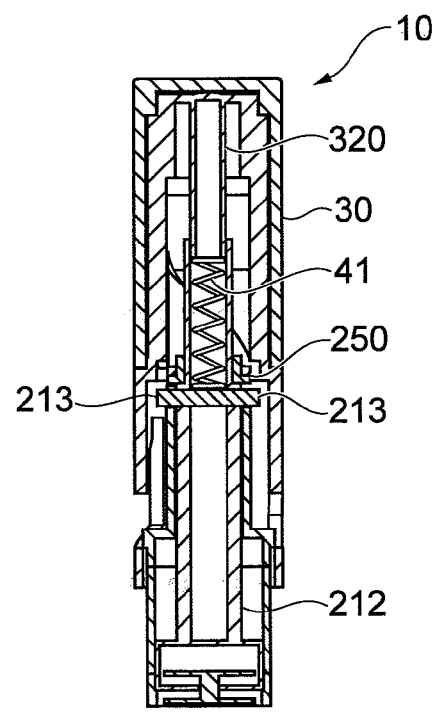
(b)
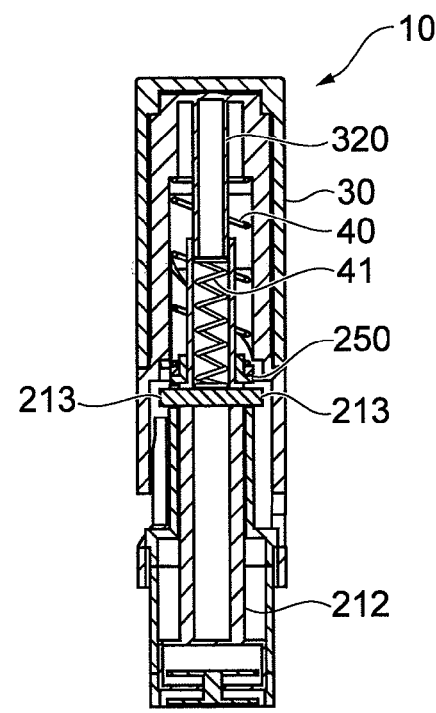

APPLICATOR

TECHNICAL FIELD

One mode of the present invention relates to an applicator used for assisting a microneedle to administer an active component.

BACKGROUND ART

There have conventionally been known applicators which impact a microneedle for administering active components transdermally, so as to apply the microneedle to a skin. For example, the following Patent Literature 1 discloses a self-actuating applicator having a housing, a piston moveable within the housing, and a cap. In this self-actuating applicator, when a spring 40 is compressed so as to store a biasing force, release catches 38 link with a top 19a of an inner cup 14 and piston stop 18, thereby securing a piston 30. Thereafter, when a user exerts a downward force on an outer cup 20, the release catches 38 bend inward and disengage from the piston stop 18, so as to actuate the piston 30, which presses a patch.

CITATION LIST

Patent Literature

Patent Literature 1: Japanese Translated International Application Laid-Open No. 2007-509706

SUMMARY OF INVENTION

Technical Problem

As thus actuated applicator disclosed in Patent Literature 1 is used again and again, the release catches 38 or piston stop 18 may wear out. The wear-out may make it difficult to transmit a desirable amount of energy to the microneedle through the piston 30 or secure the piston 30 when compressing the spring 40, whereby the applicator may fail to keep its performances. It has therefore been demanded for applicators to keep their performances for a long period of time.

Solution to Problem

The applicator in accordance with one mode of the present invention is an applicator for applying a microneedle to skin, the applicator comprising a transmission member transmitting a biasing force of an elastic member to the microneedle, a housing containing at least a part of the transmission member and guiding a reciprocation of the transmission member, and a cap disposed so as to cover the housing and adapted to impart the biasing force to the elastic member by being pressed toward the transmission member; wherein the transmission member is provided with a stopper extending in a direction orthogonal to an axial direction of the transmission member; wherein one end of the housing adapted to mount the stopper is formed with a projection guiding the stopper along one circumferential direction; wherein the inside of the cap is formed with a lead part adapted to come into contact with the stopper when the cap is pushed; and wherein the stopper is slid by the lead part to an end part of the projection when the cap is pushed toward the transmission member and thereafter disengages from the projection when the cap is further pushed toward the transmission member, so that the transmission member transmits the biasing force to the microneedle.

In this mode, when the cap is pushed toward the transmission member, the stopper of the transmission member moves while sliding in a predetermined circumferential direction at one end of the housing. When the cap is further pushed thereafter, the stopper disengages from the projection, whereby the transmission member transmits the biasing force of the elastic member to the microneedle. Thus furnishing one end of the housing with a role to keep the transmission member in such a state as to resist against the biasing force of the elastic member makes it unnecessary to provide fixing members, such as latch mechanisms, for securing the transmission member. As a result, performances of the applicator can be kept for a long period of time without causing such fixing members to wear out.

The applicator in accordance with another mode may be constructed such that, when the cap is pushed toward the transmission member, the stopper is slid by the lead part to the end part of the projection, and the transmission member separates from the microneedle against the biasing force.

The applicator in accordance with still another mode may be constructed such that a side face of the housing covered with the cap is provided with a protrusion, the cap is formed with an opening or depression receiving the protrusion, and a side of the opening or depression in contact with the protrusion when the cap is pushed toward the transmission member is inclined in a direction opposite from a sliding direction of the stopper.

Thus forming a side of the opening or depression allows the cap to rotate in the moving direction of the stopper during when the cap is pushed so that the side is in contact with the protrusion. The force caused by the rotation acts on the lead part pushing the stopper. Therefore, the user can easily move the transmission member toward the cap (the side remote from the microneedle) with a smaller force.

In the applicator in accordance with yet another mode, another side of the opening or depression may be formed so as to return the pushed cap to an initial state. This can easily return the cap to the initial state.

The applicator in accordance with a further mode may be constructed such that the cap comprises a cap body formed with the opening or depression and a grip part to be grasped by a user, wherein the cap body is rotatable with respect to the grip part. Thus separating the cap body and grip part from each other makes the gripping less susceptible to the movement of the cap body, whereby arms of the user can be prevented from being twisted when pushing the cap.

The applicator in accordance with a further mode may be constructed such that the transmission member is provided with two stoppers separated from each other by 180° on an axis orthogonal to the axial direction of the transmission member, the one end of the housing having two such projections, each projection having a inclined part extending halfway around the one end.

In the applicator in accordance with a still further mode, the lead part may have a gradient greater than that of the projection.

Thus setting the gradient of the lead part increases the force by which the lead part pushes the stopper, whereby the force caused by the user pushing the cap is efficiently transmitted to the stopper. Therefore, the user can easily move the transmission member toward the cap (the side remote from the microneedle) with a smaller force.

In the applicator in accordance with a furthermore mode, the transmission member may comprise a rod-shaped member provided with the stopper and a transmission plate disposed at one end of the rod-shaped member with a range of play in an axial direction of the rod-shaped member.

Advantageous Effects of Invention

One aspect of the present invention makes it unnecessary to provide fixing members (e.g., latch mechanisms) for securing a transmission member for transmitting a biasing force of an elastic member to a microneedle, whereby performances of the applicator can be kept for a long period of time.

BRIEF DESCRIPTION OF DRAWINGS

FIGS. 13(*a*) and 13(*b*) (corresponding to FIG. 7) are sectional views of applicators in accordance with modified examples.

DESCRIPTION OF EMBODIMENTS

In the following, preferred embodiments of the present invention will be explained in detail with reference to the accompanying drawings. In the explanation of the drawings, the same or equivalent constituents will be referred to with the same signs while omitting their overlapping descriptions.

Figure 1:
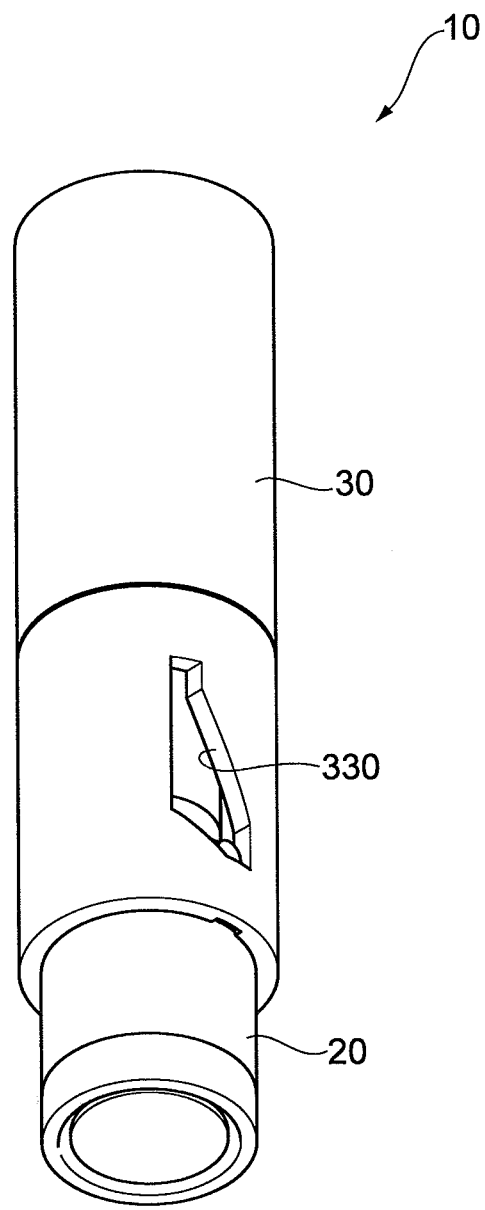
FIG. 1 is a perspective view of an applicator in accordance with an embodiment as seen from thereunder.
Figure 2:
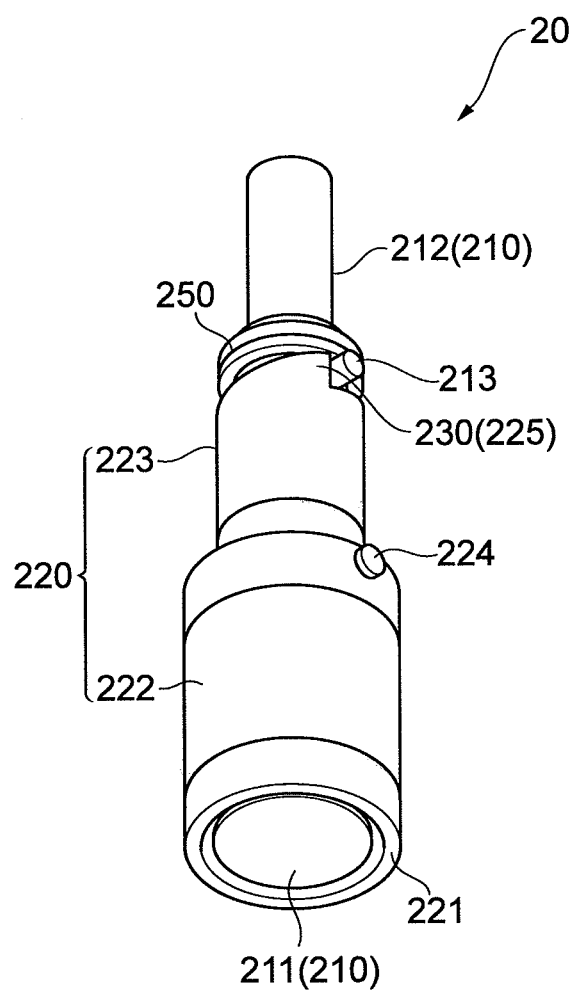
FIG. 2 is a perspective view of a main part illustrated in FIG. 1 as seen from thereunder.
Figure 3:
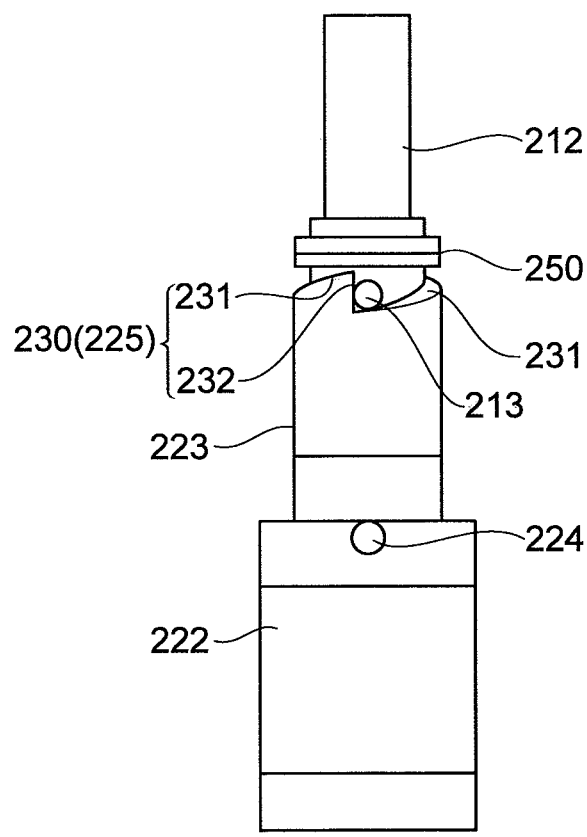
FIG. 3 is a front view of the main part illustrated in FIG. 2.
Figure 4:
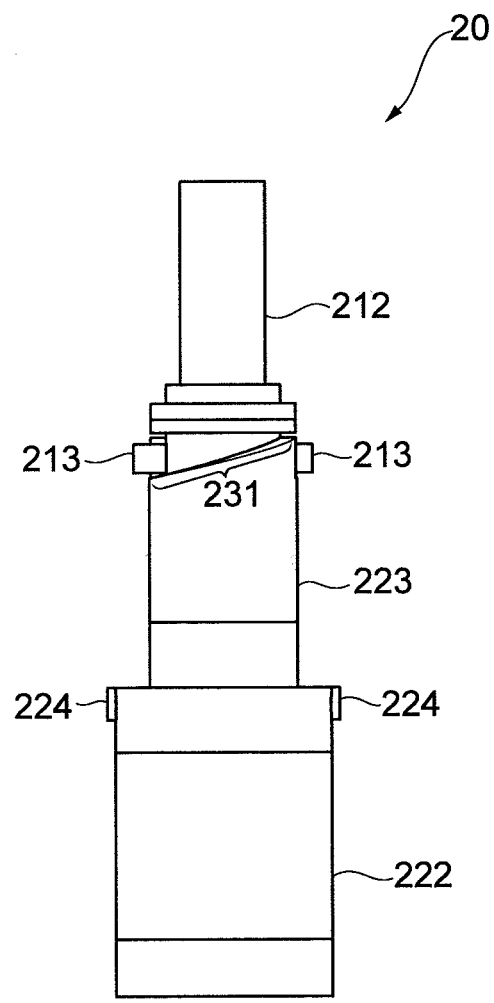
FIG. 4 is a right side view of the main part illustrated in FIG. 2.
Figure 5:
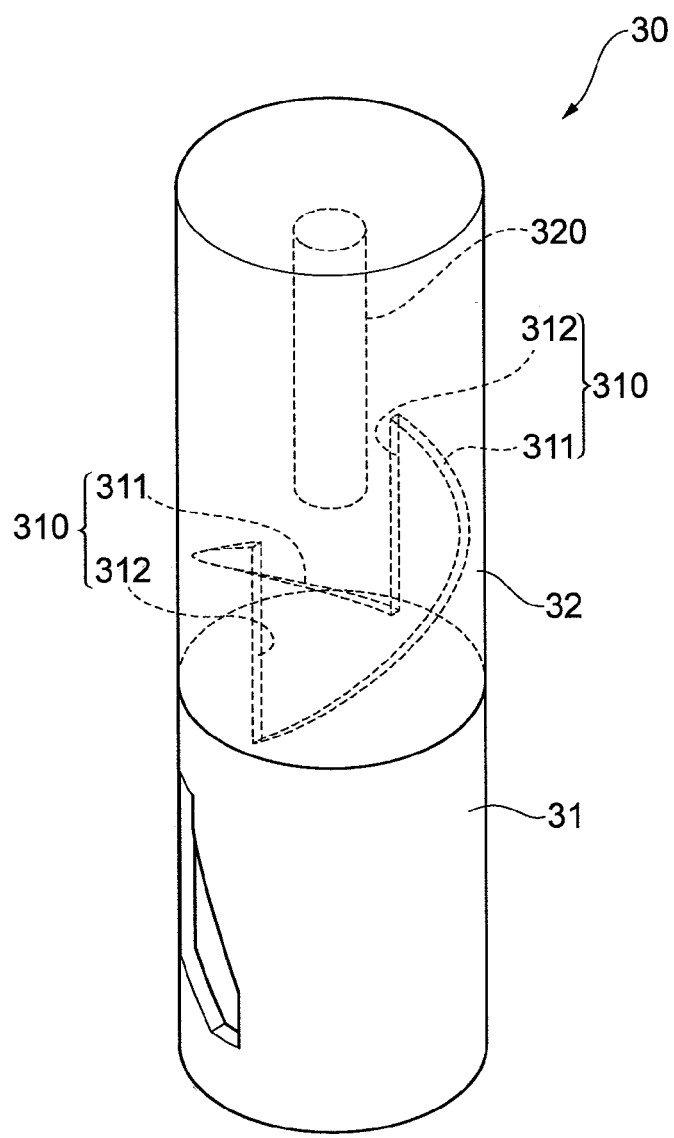
FIG. 5 is a perspective view of a cap illustrated in FIG. 1 as seen from thereabove.
Figure 6:
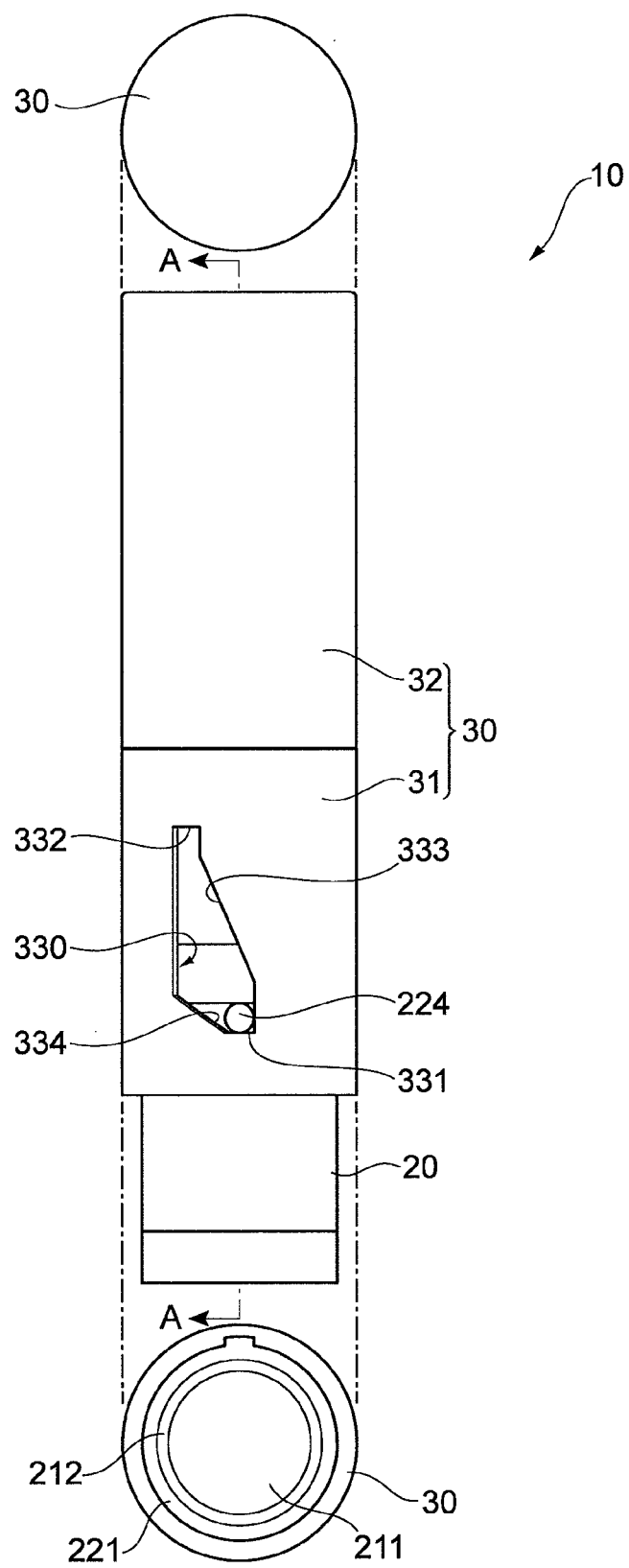
FIG. 6 is a set of front, plan, and bottom views of the applicator illustrated in FIG. 1.
Figure 7:
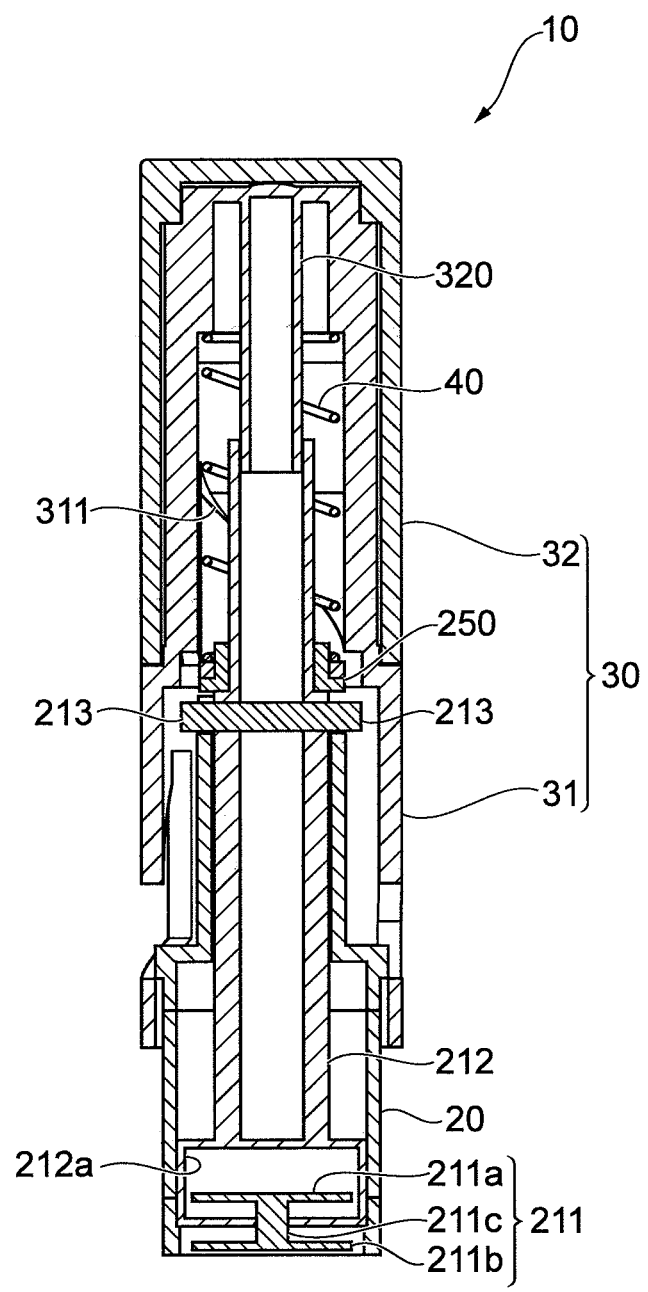
FIG. 7 is a sectional view taken along the line A-A of FIG. 6 (front view)

First, with reference to FIGS. 1 to 7, the structure of an applicator 10 in accordance with an embodiment will be explained. FIG. 1 is a perspective view of the applicator 10 as seen from thereunder. FIG. 2 is a perspective view of a main part 20 as seen from thereunder. FIG. 3 is a front view of the main part 20. FIG. 4 is a right side view of the main part 20. FIG. 5 is a perspective view of a cap 30 as seen from thereabove. FIG. 6 is a set of front, plan, and bottom views of the applicator 10. FIG. 7 is a sectional view taken along the line A-A of FIG. 6 (front view).

The applicator 10 is a cylindrical auxiliary device used for applying a microneedle to a skin. As illustrated in FIG. 1, the applicator 10 comprises a tubular main part 20 having one end adapted to come into contact with the skin when in use and a tubular cap 30 attached to the main part 20 so as to cover the other end of the main part 20. In the following, the main part 20 and cap 30 sides of the applicator 10 will be defined as the lower and upper sides thereof, respectively.

First, the main part 20 will be explained with reference to FIGS. 2 to 4, 6, and 7. The main part 20 comprises a columnar transmission member 210 for imparting a biasing force of a spring 40 to the microneedle put on the skin and a tubular housing 220 for containing the transmission member 210 and guiding reciprocations of the transmission member 210.

The transmission member 210 is constituted by a transmission plate 211 adapted to collide with the microneedle and a cylindrical rod-shaped member 212 extending in a direction orthogonal to a surface of the transmission plate 211.

The transmission plate 211 is constituted by first and second plate parts 211*a*, 211*b* opposing each other and a circular columnar joint 211*c* connecting the plate parts to each other (see FIGS. 2 and 7). The first and second plate parts 211*a*, 211*b* are shaped into discs.

Two stoppers 213 extending in a direction orthogonal to the axial direction of the rod-shaped member 212 (i.e., the axial direction of the transmission member 210) are disposed in the middle of the rod-shaped member 212. The two stoppers 213 are actualized by one axial member penetrating through the rod-shaped member 212 diametrically and thus are separated from each other by 180° on one orthogonal axis (see FIG. 4). A space (container) 212*a* for containing the first plate part 211*a* of the transmission plate 211 is formed at the lower end of the rod-shaped member 212 (see FIG. 7). In this embodiment, as illustrated in FIG. 7, the transmission plate 211 (second plate part 211*b*) has a diameter smaller than that of the lower end of the rod-shaped member 212, so that a part of the lower end of the rod-shaped member 212 can be seen as illustrated in FIG. 6 (bottom view) when the applicator 10 is observed from thereunder.

The transmission plate 211 is not secured to the rod-shaped member 212 but disposed at the lower end part of the rod-shaped member 212 with a play in the axial direction of the rod-shaped member 212. Therefore, the transmission plate 211 is movable in the axial direction of the rod-shaped member 212. However, the movable range (range of play) of the transmission plate 211 with respect to the rod-shaped member 212 is limited to a range in which the first plate part 211*a* is movable within the container 212*a*.

The transmission plate 211, thus caught on the rod-shaped member 212, moves up when the rod-shaped member 212 does so. When the transmission member 210 is actuated by the spring 40, which will be explained later, the rod-shaped member 212 initially collides with the second plate part 211*b* of the transmission plate 211, and then the rod-shaped member 212 and transmission plate 211 move down together. Thereafter, the lower end (container 212*a*) of the rod-shaped member 212 stops at a part higher than the lower end 221 of the applicator 10, while the transmission plate 211 keeps descending under the inertial force, thereby transmitting the biasing force of the spring 40 to the microneedle.

The housing 220 covers a part of the transmission member 210 from the transmission plate 211 to the stoppers 213. The lower end 221 of the housing 220 is in contact with the skin when the applicator 10 is in use, while the transmission plate 211 is located near the lower end 221. The housing 220 is formed into a two-stage nest in which a lower stage 222 has a diameter greater than that of an upper stage 223. The upper end of the side face of the lower stage 222 is provided with two protrusions 224 which are separated from each other by 180° (see FIG. 4). The protrusions 224 have a circular cross section.

The upper end 225 of the housing 220 has two saw-toothed projections 230. Each projection 230 is constituted by a inclined part (first inclined part) 231 helically inclined half around (in the range of) 180° and a wall part 232 cut along the axial direction of the housing 220 from the top of the inclined part 231 (see FIG. 3). When the main part 20 is seen from thereabove, the inclined part 231 rises counterclockwise (along one circumferential direction). As illustrated in FIG. 2, the stoppers 213 of the rod-shaped member 212 are mounted on the upper end 225 of the housing 220. The stoppers 213 abut the respective wall parts 232 when having no external force applied thereto (see FIG. 3).

An annular member 250 for mounting the lower end of the spring 40 is further positioned at the upper end 225 side of the housing 220 containing the transmission member 210. Since the annular member 250 has substantially the same diameter as with the upper stage 223 of the housing 220, the leading end parts of the stoppers 213 are exposed when the main part 20 is seen from thereabove (see FIG. 4).

The cap 30 will now be explained with reference to FIGS. 5 to 7. The cap 30 is constituted by a cap body 31 formed into a two-stage nest in which a lower stage has a diameter greater than that of an upper stage (see FIG. 7) and a grip part 32 put on the cap body 31 so as to cover the upper stage. The outer diameter of the grip part 32 conforms to that of the lower stage of the cap body 31. The cap body 31 is rotatable with respect to the grip part 32.

The inner wall of the upper stage of the cap body 31 is formed with two saw-toothed stopper lead parts 310 adapted to come into contact with the stoppers 213 when the cap 30 is pushed toward the main part 20. Each stopper lead part 310 is constituted by a inclined part (second inclined part) 311 helically inclined half around (in the range of 180°) and a wall part 312 cut along the axial direction of the cap 30 from the top of the inclined part 311. One stopper lead part 310 corresponds to one projection 230. The inclined parts 311 rise counterclockwise, as with the inclined parts 231 of the projections 230, when the main part 20 is seen from thereabove. The gradient of the inclined parts 311 (gradient of the stopper lead parts 310) is greater than that of the inclined parts 231 (gradient of the projections 230). The center part of the upper wall of the cap body 31 is provided with a tubular spring guide 320 extending along the axial direction of the cap body 31.

As illustrated in FIG. 6 (front view), the side face of the lower stage of the cap body 31 is formed with two substantially trapezoidal openings 330 corresponding to the two protrusions 224 of the housing 220, respectively. The two openings 330 are separated from each other by 180°. Among the sides constructing each opening 330, a pair of opposite sides parallel to each other extend along the axial direction of the cap body 31 (cap 30), while the remaining pair of opposite sides, i.e., upper and lower sides 333, 334, rise clockwise along the outer wall of the cap body 31 when the cap body 31 is seen from thereabove (see also FIG. 1). Hence, the upper side 333 inclines in a direction opposite from that of the inclined parts 231, 311 (i.e., in a direction opposite from the sliding direction of the stoppers 213). The lowermost part 331 of the opening 30 is chamfered so as to mount the protrusion 224, while the uppermost part 332 of the opening 330 is formed into a cutout having such a size as to contain the protrusion 224.

The spring 40, which is an elastic member for imparting a predetermined amount of kinetic energy to the transmission member 210, is a compression spring adapted to store energy when compressed. The spring 40, which is circular columnar, is put into the cap 30 (more specifically within the cap body 31) so as to surround the spring guide 320, while the upper and lower ends of the spring 40 are in contact with the upper wall of the cap body 31 and the annular member 250, respectively.

Parameters concerning the energy of the transmission member 210 actuated by the biasing force of the spring 40 include the modulus of transverse elasticity, wire diameter, number of windings, average coil diameter, distance indicating how much the spring 40 can be compressed from its natural length, velocity, mass of the spring, and mass of the transmission member.

The modulus of transverse elasticity is determined by the material of the spring, e.g., 68500 N/m² for stainless steel and 78500 N/m² for piano wires (iron). The other parameters may be determined in view of the desired biasing force, size of the applicator 10, and the like.

Using the above-mentioned parameters, theoretical formulas concerning the spring are defined as follows. Expression (1) represents the relationship among the spring constant, spring form, and material, while expression (2) indicates the relationship between the mass and size of the spring. Expression (3) represents the relationship between the spring energy and kinetic energy, while expression (4) indicates the relationship among the velocity, energy (E), and mass of the spring. In the following expressions, G is the modulus of transverse elasticity (N/m²), d is the wire diameter (m), n is the number of windings, D is the average coil diameter (m), k is the spring constant (N/m), x is the distance (m), v is the velocity (m/s), l is the length of the spring when expanded (m), ρ is the density (kg/m³), m is the mass of the spring (kg), and M is the mass of the transmission member (kg).

[Math. 1]

$$k = \frac{Gd^4}{8nD^3} \quad (1)$$

[Math. 2]

$$m = \frac{\rho \pi l d^2}{4} \quad (2)$$

[Math. 3]

$$E = \frac{1}{2}kx^2 \quad (3)$$
$$= \frac{1}{2}Mv^2$$

[Math. 4]

$$v = \sqrt{\frac{2E}{M}} \quad (4)$$

The puncture property of the applicator depends on the mass and velocity of the transmission member. Changing the masses of the first and second plate parts 211a, 211b can vary the collision parameters without altering the applicator main part.

The size of the applicator 10 may be determined according to the size of the microneedle. For example, conforming the form of the lower end 221 of the housing 220 to that of the microneedle and the inner diameter of the lower end 221 to the outer diameter of the microneedle can make the applicator 10 smaller. Thus shaping the lower end 221 prevents the applicator 10 from shifting diametrically (widthwise) with respect to the microneedle when positioning the applicator 10 on the microneedle. Therefore, while keeping a parallel positional relationship with the microneedle, the biasing force of the spring 40 can be transmitted to the microneedle through the transmission member 210. This makes it possible to perform punctures securely (increase the reproducibility of punctures). These do not restrict how to determine the size, however.

Though materials for the applicator are not limited in particular, those having such a strength as to keep the biasing force of the spring 40 are desirable. For example, synthetic and natural resin materials such as ABS resins, polystyrene, polypropylene, and polyacetal (POM) resins, as well as silicon, silicon dioxide, ceramics, and metals (stainless steel, titanium, nickel, molybdenum, chromium, cobalt, etc.) may be used. Among them, polyacetal (POM) resins are most preferred in view of the slidability of the applicator. The transmission member 210 may be produced by using the same material as with the microneedle.

Figure 8:
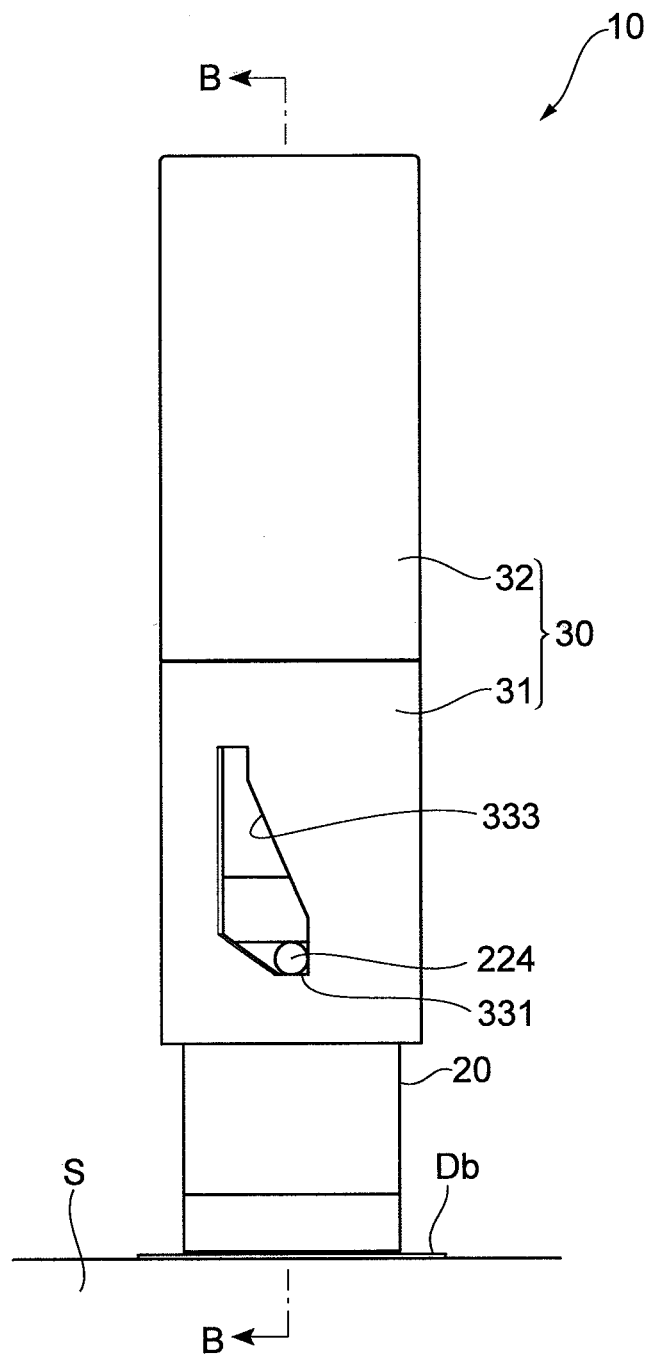
FIG. 8 is a diagram illustrating an initial state of the applicator illustrated in FIG. 1 when in use.
Figure 9:
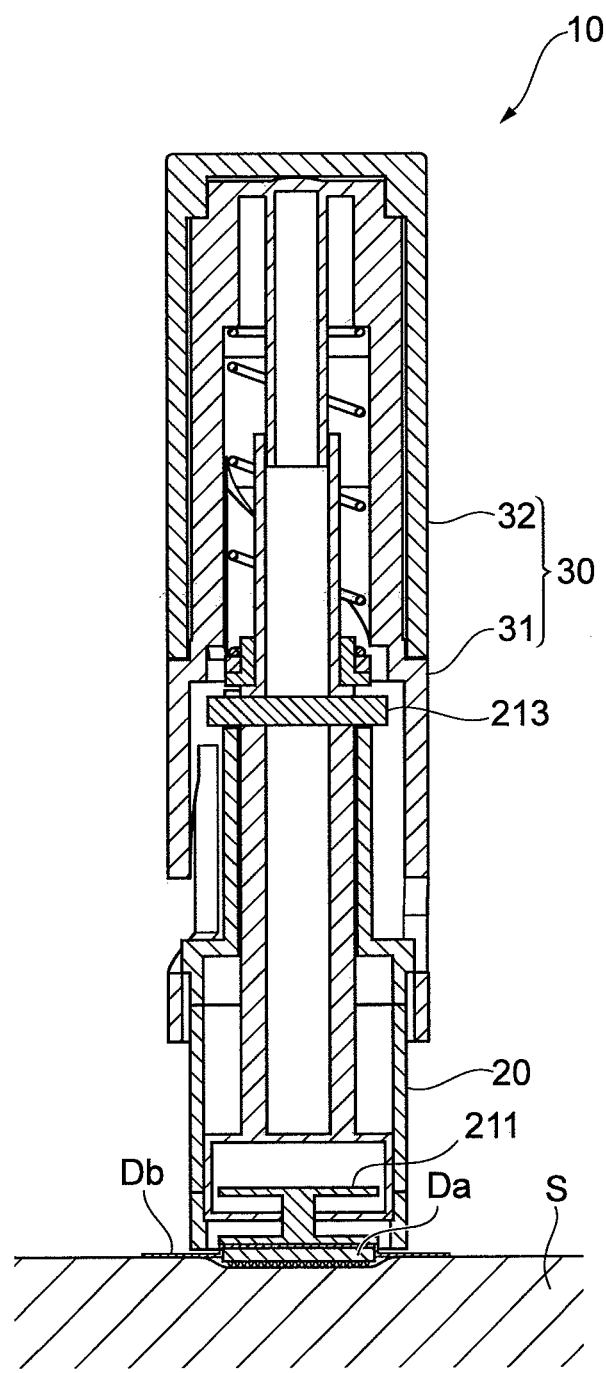
FIG. 9 is a sectional view taken along the line B-B of FIG. 8.
Figure 10:
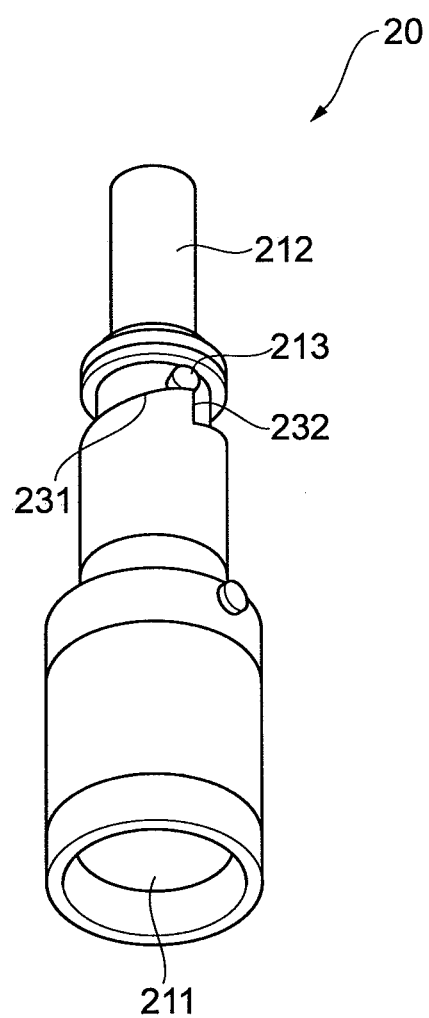
FIG. 10 is a diagram illustrating a state where a transmission member is raised.
Figure 11:
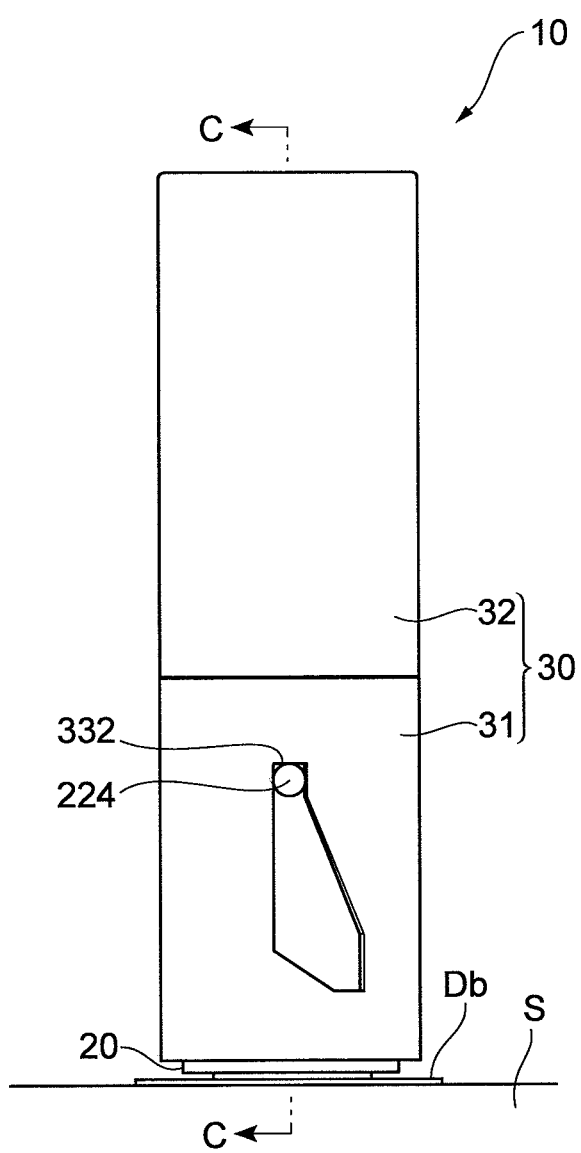
FIG. 11 is a diagram illustrating a state of the applicator when the transmission member is in action.
Figure 12:
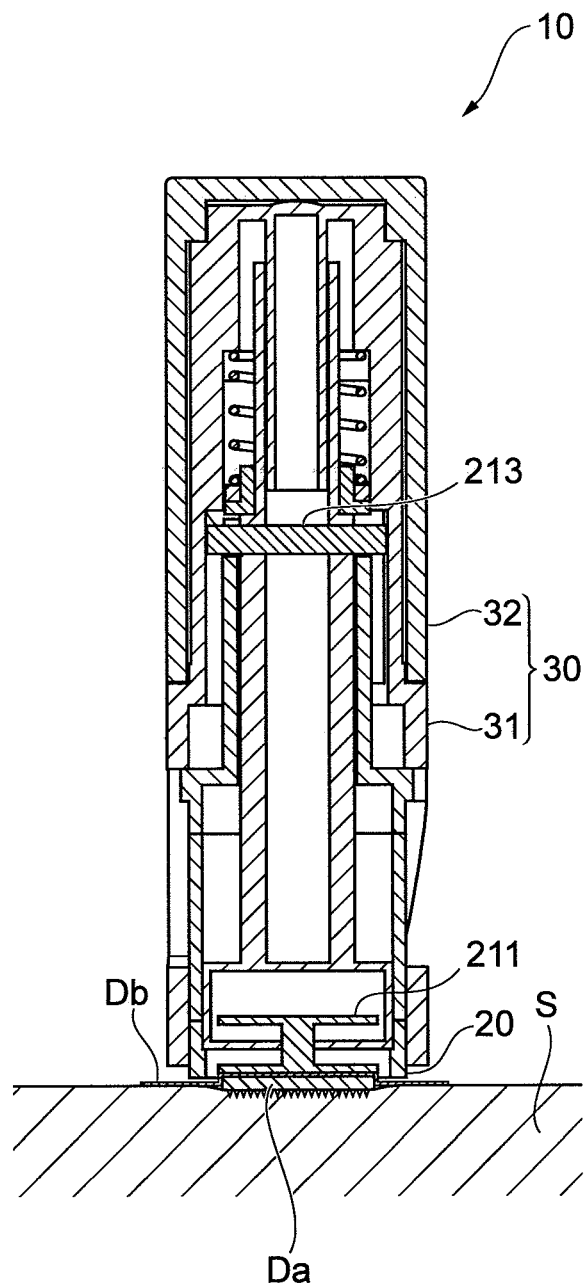
FIG. 12 is a sectional view taken along the line C-C of FIG. 11.

A method of using the applicator 10 will now be explained with reference to FIGS. 8 to 12. FIG. 8 is a diagram illustrating an initial stage of the applicator 10 when in use. FIG. 9 is a sectional view taken along the line B-B of FIG. 8. FIG. 10 is a diagram illustrating a state where the transmission member 210 is raised. FIG. 11 is a diagram illustrating a state of the applicator 10 when the transmission member 210 is in action. FIG. 12 is a sectional view taken along the line C-C of FIG. 11.

The initial state of the applicator 10 is as illustrated in FIGS. 8 and 9. In the initial state, the spring 40 is expanded, so that the cap 30 is raised to a position at which the lowermost parts 331 of the opening 330 abut the protrusions 224. The stoppers 213 abut the wall parts 232 of the upper end 225 of the housing 220 (see FIGS. 2 to 4), while the transmission plate 211 is located at the lower end of the housing 220.

First, the applicator 10 is positioned and held on a microneedle Da put on a skin S and, while the grip part 32 is held, the cap 30 is pushed toward the skin S. Before positioning the applicator 10, the microneedle Da may be attached to the skin with a cover material Db (see FIG. 9). The transmission plate 211 may hold the microneedle, so that the microneedle is incorporated in the applicator 10.

When the user starts pushing the cap 30, the spring 40 begins to contract, thereby commencing to store the biasing force. The stopper lead parts 310 within the cap 30 move down, so that the stoppers 213 begin to slide on the inclined parts 231.

When the user keeps pushing the cap 30 as it is, the upper sides 333 of the openings 330 come into contact with the protrusions 224 and then move down while in contact with the protrusions 224, whereby the cap body 31 rotates counterclockwise as seen from above the applicator 10. At this time, the stoppers 213, each held between the inclined part 231 of the upper end 225 of the housing 220 and the inclined part 311 of the stopper lead part 310 of the cap body 31, slide upward along the inclined parts 231 as being pushed by the stopper lead parts 310 of the rotating cap body 31. Therefore, the transmission member 210 moves up while rotating. As for the cap 30, only the cap body 31 rotates, while the grip part 32 grasped by the user does not rotate.

At the time when the stoppers 213 reach the tops of the inclined parts 231 as illustrated in FIG. 10, the spring 40 stores a desirable biasing force for causing the transmission member 210 to collide with the microneedle. Since the stoppers 213 are still mounted on the inclined parts 231, however, the transmission member 210 keeps a state raised by a predetermined distance from the lower end 221 of the housing 220 against the biasing force.

When the user further pushes the cap 30 in such a state, the stoppers 213 further rotate counterclockwise as seen from above the applicator 10 and disengage from the inclined parts 231. As a consequence, the transmission member 210 loses its support and is moved to the lower side of the applicator 10 by the biasing force of the spring 40 (while the stoppers 213 move down along the wall parts 232), thereby colliding with the microneedle Da as illustrated in FIGS. 11 and 12. This collision causes the needle part of the microneedle Da to puncture the stratum corneum of the skin, whereby an active component applied to the microneedle Da is administered into the body through the needle part. At this time, the protrusions 224 abut the uppermost parts 332 of the openings 330 as illustrated in FIG. 11, thereby keeping the cap 30 from descending more. Since the stoppers 213 are remounted on the upper end 225 of the housing 220 while in contact with the wall parts 232, the transmission member 210 does not descend from the lower end 221 of the housing 220.

As mentioned above, after the rod-shaped member 212 and transmission plate 211 move down together, the lower end (container 212a) of the rod-shaped member 212 stops at a part higher than the lower end 221 of the applicator 10, while the transmission plate 211 keeps dropping under the inertial force. The transmission plate 211 transmits the biasing force of the spring 40 to the microneedle. Therefore, in a strict sense, the transmission plate 211 transmits the biasing force of the spring 40 to the microneedle not directly but indirectly.

When the user stops pushing down the cap 30 after thus using the applicator 10, the cap 30 moves up under the stretching force of the spring 40 until the lowermost parts 331 of the openings 330 abut the protrusions 224. At this time, the lower sides 334 of the openings 330 come into contact with the protrusions 224, thereby guiding the lowermost parts 331 to the protrusions 224. This allows the applicator 10 to return to the initial state illustrated in FIGS. 8 and 9. Therefore, when using the applicator 10 next time, it will be sufficient if the applicator 10 returned to the initial state is positioned and held on another microneedle, and then the cap 30 is pushed toward the skin. Hence, the applicator 10 is a self-actuating applicator.

When the cap 30 is pushed toward the transmission member 210 in this embodiment, as explained in the foregoing, the stoppers 213 of the rod-shaped member 212 move along the inclined parts 231 of the upper end 225 of the housing 220, whereby the transmission member 210 goes away from the microneedle against the biasing force of the spring 40. When the cap 30 is further pushed thereafter, the stoppers 213 disengage from the inclined parts 231, whereby the transmission member 210 transmits the biasing force of the spring 40 to the microneedle. As a consequence, the microneedle is applied to the skin. Thus furnishing one end of the housing 220 with a role to keep the transmission member 210 in such a state as to resist against the biasing force of the spring 40 makes it unnecessary to provide fixing members, such as latch mechanisms, for securing the transmission member 210. As a result, performances of the applicator 10 can be kept for a long period of time without causing such fixing members to wear out. The applicator 10 can also be called a latchless applicator.

Since the transmission member 210 is actuated only when the stoppers 213 disengage from the inclined parts 231, the biasing force transmitted to the microneedle becomes constant no matter who administers it. This makes it possible to perform punctures securely (increase the reproducibility of punctures).

When the cap 30 is pushed so that the upper sides 333 of the openings 330 are in contact with the protrusions 224, the cap 30 (more specifically the cap body 31) rotates in such a direction that the inclined parts 231, 311 rise. The force caused by the rotation acts on the inclined parts 311 pushing the stoppers 213. Therefore, the user can easily move up the transmission member 210 with a smaller force. At the time of this operation, only the cap body 31 rotates, but the grip part 32 grasped by the user does not rotate, whereby arms of the user are prevented from being twisted while pushing the cap 30. The applicator 10 is user-friendly also from this point.

In this embodiment, the gradient of the inclined parts 311 is greater than that of the inclined parts 231, whereby the force by which the inclined parts 311 push the stoppers 213 (the force acting in the direction along the inclined parts 231) increases. Therefore, the force produced by the user pushing the cap 30 is more efficiently transmitted to the stoppers 213. Hence, the user can easily move up the transmission member 210 with a smaller force.

The applicator 10 is advantageous over the self-actuating applicator disclosed in the above-mentioned Patent Literature 1 not only in that it is latchless, but also in that only one spring is necessary therefor. Specifically, the self-actuating applicator disclosed in the above-mentioned Patent Literature 1 necessitates two springs, i.e., an impact spring and a presetting spring, by which the applicator must become larger in scale. By contrast, it is sufficient for the applicator 10 to prepare one spring 40 as an elastic member, by which the applicator 10 can be made smaller.

The present invention is explained in detail according to its embodiments in the foregoing. However, the present invention is not limited to the above-mentioned embodiment. The present invention can be modified in various ways within the scope not deviating from the gist thereof.

The form of the opening 330 may be determined arbitrarily in view of designability and the like as long as a side having a function equivalent to that of the upper side 333 is provided.

While the openings 330 are formed in the lower stage of the cap body 31 in the above-mentioned embodiment, the inner wall of the lower stage of the cap body 31 may be formed with depressions having a form identical or equivalent to that of the openings 330 without making holes at parts coming into contact with the protrusions 224. During when the cap 30 is pushed so that the upper sides of the depressions are in contact with the protrusions 224, the cap body 31 rotates in such a direction that the inclined parts 231, 311 rise. The force produced by the rotation acts on the inclined parts 311 pushing the stoppers 213. Therefore, the user can easily move up the transmission member 210 with a smaller force. When a depression is formed, its edges do not appear on the outer surface of the cap, whereby a case where such a design is desired can be dealt with.

While the applicator 10 has a cylindrical form in the above-mentioned embodiment, the outer form of the applicator is not limited thereto. For example, the applicator may have a polygonal cross section, a rounded outer wall as a whole, or a depressed or stepped outer wall in order to make the applicator easier to grasp or the microneedle easily applicable to the skin. The surface of the outer wall may be formed with fine grooves or provided with a coating in order to make it harder to slip.

The cap 30 and transmission member 210 may be provided with air holes for letting the air out, so as to lower the air resistance and reduce the weight.

Though the above-mentioned embodiment is provided with two stoppers 213 and their corresponding two projections 230 and two stopper lead parts 310, the number of stoppers is not limited thereto. For example, while providing one stopper, the projection and stopper lead part may be formed one by one. In this case, each of the inclined parts on the housing and cap sides is formed by 360°. While providing four stoppers at intervals of 90°, four projections and four stopper lead parts may be formed. In this case, each of the inclined parts on the housing and cap sides is formed by 90°. While providing three stoppers at intervals of 120°, three projections and three stopper lead parts may be formed. In this case, each of the inclined parts on the housing and cap sides is formed by 120°.

The gradients of the inclined parts 231, 311 in the above-mentioned embodiment may be determined arbitrarily as long as the gradient of the inclined parts 311 (on the cap 30 side) is not smaller than that of the inclined parts 231 (on the housing 220 side). The gradients of the inclined parts and the number of stoppers mentioned above may be set in view of the operability of the applicator.

The mode of installing the spring is not limited to that of the above-mentioned embodiment. For example, as illustrated in (a) of FIG. 13, a circular columnar spring 41 may be inserted in the rod-shaped member 212. In this case, the lower end of the spring 41 is in contact with an axial member for actualizing the stoppers 213, while the upper end of the spring 41 is in contact with the spring guide 320. As illustrated in (b) of FIG. 13, both of the two springs 40, 41 mentioned above may also be used.

The form of the spring is not limited, and a conical spring may be used, for example. This can suppress the length in the expansion/contraction direction of the spring at the time of compression, so as to restrict the axial size of the applicator, thereby making the applicator smaller in size and lighter in weight.

While the spring 40 is used in the above-mentioned embodiment, elastic members other than springs may also be used.

The transmission plate 211, which is attached to the rod-shaped member 212 with a play, may be secured to the rod-shaped member 212. For example, the transmission plate 211 and rod-shaped member 212 may be formed integrally.

While the cap 30 is designed such that the cap body 31 is rotatable with respect to the grip part 32, a cap in which a cap body and a grip part are integrated may also be employed.

REFERENCE SIGNS LIST

10 . . . applicator; 20 . . . main part; 30 . . . cap; 40 . . . spring; 210 . . . transmission member; 211 . . . transmission plate; 211a . . . first plate part; 211b . . . second plate part; 211c . . . joint; 212 . . . rod-shaped member; 213 . . . stopper; 220 . . . housing; 224 . . . protrusion; 225 . . . upper end of the housing; 230 . . . projection; 231 . . . inclined part on the housing side; 232 . . . wall part on the housing side; 250 . . . annular member; 310 . . . stopper lead part; 311 . . . inclined part on the cap side; 312 . . . wall part on the cap side; 320 . . . spring guide; 330 . . . opening; 333 . . . upper side of the opening (a side of the opening in contact with the protrusion when the cap is pushed toward the transmission member); 334 . . . lower side of the opening (another side of the opening formed so as to return the pushed cap to an initial state)

The invention claimed is:

1. An applicator for applying a microneedle to skin, the applicator comprising:
    a transmission member for transmitting a biasing force of an elastic member to the microneedle;
    a housing containing at least a part of the transmission member and guiding a reciprocation of the transmission member; and
    a cap disposed so as to cover the housing and adapted to impart the biasing force to the elastic member by being pressed toward the transmission member;
    wherein the transmission member is provided with a stopper extending in a direction orthogonal to an axial direction of the transmission member;
    wherein one end of the housing adapted to mount the stopper is formed with a projection guiding the stopper along one circumferential direction;
    wherein an inside of the cap is formed with a lead part adapted to come into contact with the stopper when the cap is pushed; and wherein the stopper is slid by the lead part to an end part of the projection when the cap is pushed toward the transmission member and thereafter disengages from the projection when the cap is further pushed toward the transmission member, so that the transmission member transmits the biasing force to the microneedle.

2. The applicator according to claim 1, wherein, when the cap is pushed toward the transmission member, the stopper is slid by the lead part to the end part of the projection, and the transmission member separates from the microneedle against the biasing force.

3. The applicator according to claim 1, wherein a side face of the housing covered with the cap is provided with a protrusion;
wherein the cap is formed with an opening or depression for receiving the protrusion; and
wherein a side of the opening or depression in contact with the protrusion when the cap is pushed toward the transmission member is inclined in a direction opposite from a sliding direction of the stopper.

4. The applicator according to claim 3, wherein another side of the opening or depression is formed so as to return the pushed cap to an initial state.

5. The applicator according to claim 3, wherein the cap comprises a cap body formed with the opening or depression and a grip part to be grasped by a user; and
wherein the cap body is rotatable with respect to the grip part.

6. The applicator according to claim 1, wherein the transmission member is provided with two stoppers separated from each other by 180° on an axis orthogonal to the axial direction of the transmission member; and
wherein the one end of the housing has two such projections, each projection having a inclined part extending halfway around the one end.

7. The applicator according to claim 1, wherein the lead part has a gradient greater than that of the projection.

8. The applicator according to claim 1, wherein the transmission member comprises a rod-shaped member provided with the stopper and a transmission plate disposed at one end of the rod-shaped member with a range of play in an axial direction of the rod-shaped member.

* * * * *